(12) United States Patent
Kong et al.

(10) Patent No.: US 7,018,996 B2
(45) Date of Patent: Mar. 28, 2006

(54) ANTIBIOTICS AW998A, AW998B, AW998C AND AW998D

(75) Inventors: Fangming Kong, River Vale, NJ (US); Guy Thomas Carter, New City, NY (US); Scott William Luckman, Ringwood, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 1 day.

(21) Appl. No.: 10/618,520

(22) Filed: Jul. 11, 2003

(65) Prior Publication Data

US 2004/0014646 A1 Jan. 22, 2004

Related U.S. Application Data

(60) Provisional application No. 60/395,766, filed on Jul. 12, 2002.

(51) Int. Cl.
 *A61K 38/12* (2006.01)
 *C07K 7/64* (2006.01)
 *C07D 401/00* (2006.01)

(52) U.S. Cl. .......... 514/183; 514/9; 530/317; 540/480; 540/481

(58) Field of Classification Search .......... 540/480, 540/481; 514/9, 183; 530/317
See application file for complete search history.

(56) References Cited

U.S. PATENT DOCUMENTS 3,126,317 A  3/1964  Heinemann et al.
4,414,206 A  11/1983  Gordon et al.

FOREIGN PATENT DOCUMENTS

WO  WO 02/05838 A1  1/2002

OTHER PUBLICATIONS

Kong et al. "Structure determination . . . " J. Antibiotics v. 56(6) 557-564 (2003).*
M. Bodanszky, et al.; J. Amer.Chem. Soc.; 95:7, pp. 2352-2357 (1973).
L. Vertesy, et al.; J. Antibiotics 53, No. 8, pp. 816-827 (2000).
Fujino, M.; Chem. Soc. Japan, 38, pp. 517-522 (1965).
Berge, et al.; J. Pharm. Sci. 66, p. 1, (1977).

* cited by examiner

Primary Examiner—Celia Chang
(74) Attorney, Agent, or Firm—Daniel B. Moran

(57) ABSTRACT

This invention relates to antibiotics selected from the group AW998A, AW998B, AW998C and AW998D derived from the microorganism *Streptomyces* designated LL-AW998, which are useful as antibacterial agents.

9 Claims, 4 Drawing Sheets

ANTIBIOTICS AW998A, AW998B, AW998C AND AW998D

"This application claims priority from copending provisional application, Application No. 60/395,766 filed Jul. 12, 2002, the entire disclosure of which is hereby incorporated by reference".

FIELD OF THE INVENTION

This invention relates to new antibiotics designated AW998A, AW998B, AW998C and AW998D, to their production by fermentation, to methods for their recovery and concentration from crude solutions and to processes for their purification. The present invention includes within its scope the agents in dilute form, as crude concentrates, as a complex of all components, in pure form as individual components and a novel strain of *Streptomyces* designated LL-AW998 and to the pharmaceutically acceptable salts thereof.

BACKGROUND OF THE INVENTION

Cyclopeptide antibiotics described in the literature include: M. Bodanszky et al. J. Amer. Chem. Soc., 95:7, 2352–2357 (1973), structure of the peptide antibiotic Amphomycin; L. Vertesy et al, J. Antibiotics 53, No. 8, 816–827 (2000), Friulimicins and Fujino, M., Bull. Chem. Soc. Japan, 38, 517–522 (1965), Glumamycin.

Reported in U.S. Pat. No. 3,126,317 is Amphomycin as a linear lipopeptide. Further reported in U.S. Pat. No. 4,414,206 is the use of Amphomycin as a feed additive.

Amphomycin previously disclosed to be a non-cyclic structure has recently been determined to be cyclic(L. Vertesy et al., J. Antibiotics, 53, No. 8, 816–827, (2000)).

BRIEF SUMMARY OF THE INVENTION

The invention relates to new antibiotics AW998A, AW998B, AW998C, and AW998D, to the production of these antibiotics by fermentation, to methods for the recovery and concentration of these antibiotics from crude solutions, and to processes for the purification of the antibiotics as well as a new microorganism useful in the preparation of these compounds.

The invention includes within its scope the new antibiotics in diluted form, as crude concentrates and in pure form. The novel antibiotics are useful as antibacterial agents.

The new antibiotics designated AW998A, AW998B, AW998C, and AW998D are formed during the cultivation under controlled conditions of a new microorganism of *Streptomyces* designated LL-AW998.

DETAILED DESCRIPTION OF THE INVENTION

The structure of the new antibiotic AW998A is

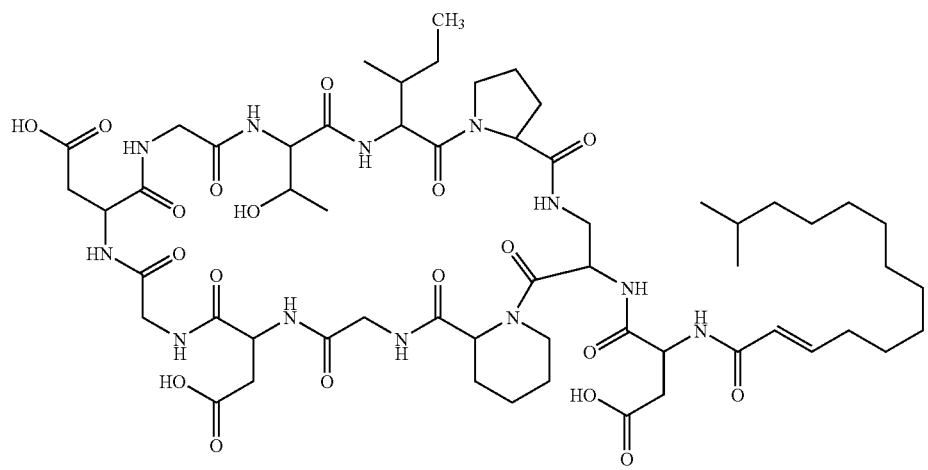

Figure 1:
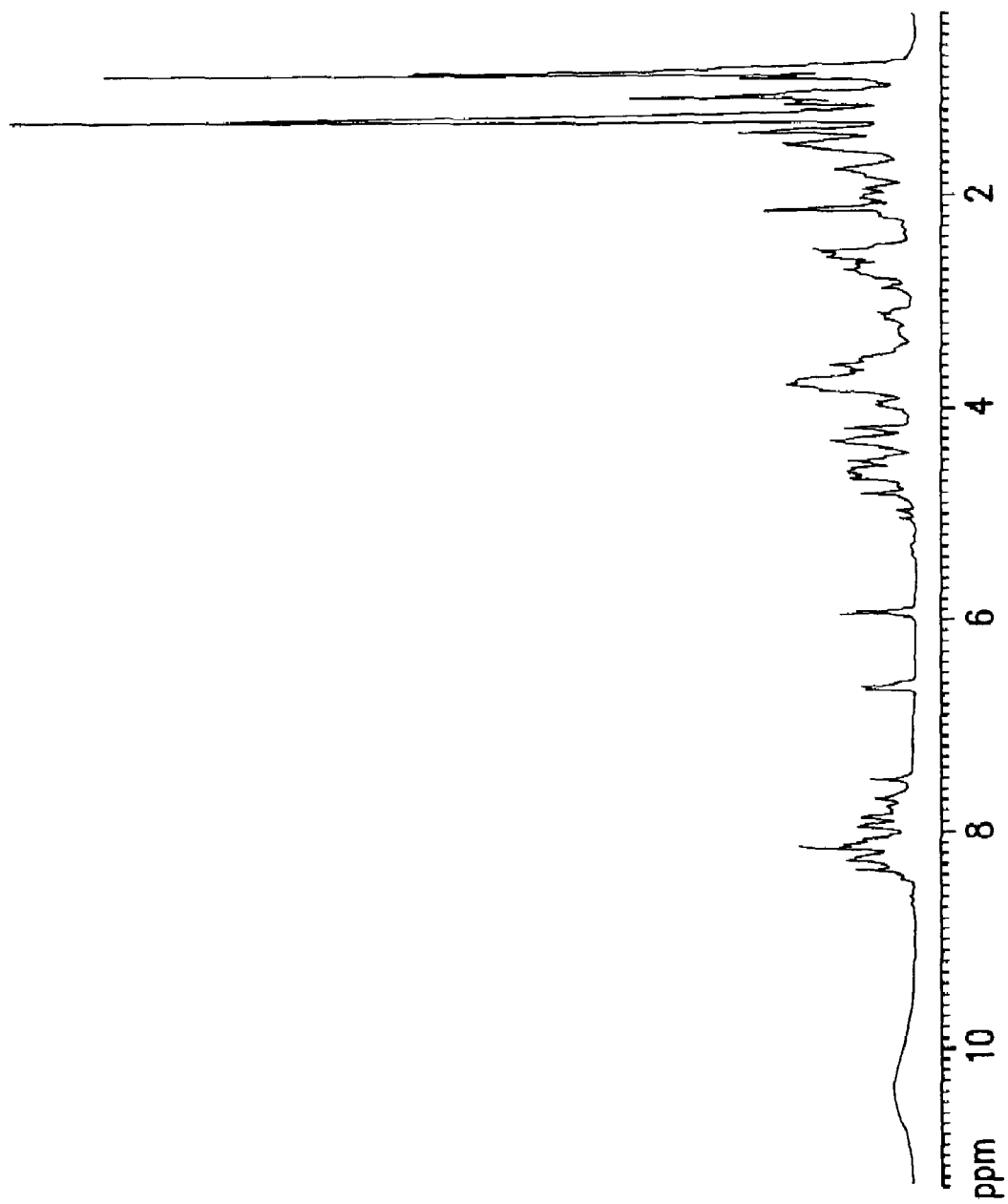
FIG. 1. Characteristic proton nuclear magnetic resonance (NMR) spectrum of compound designated AW998A in DMSO-$d_6$ at 500 MHz.

The physicochemical characteristics of AW998A are as follows:
a) Apparent Molecular Formula: $C_{57}H_{90}N_{12}O_{19}$
b) Molecular Weight: Positive Ion Electrospray MS m/z=1247.7 (M+H)$^+$; 625.0 (M+2H)$^{2+}$; High Resolution FT-MS: m/z 1247.6526 (M+H)$^+$, calculated 1247.6518
c) Ultraviolet Absorption Spectrum: $\lambda_{max}$ nm (acetonitrile-water): end absorption
d) Specific Rotation: $[\alpha]_D^{25}$=−22° (c 0.68, MeOH)
e) Proton nuclear magnetic resonance spectrum: (500 MHz DMSO-d$_6$) as shown in FIG. 1.

The structure of the new antibiotic AW998B is

Figure 2:
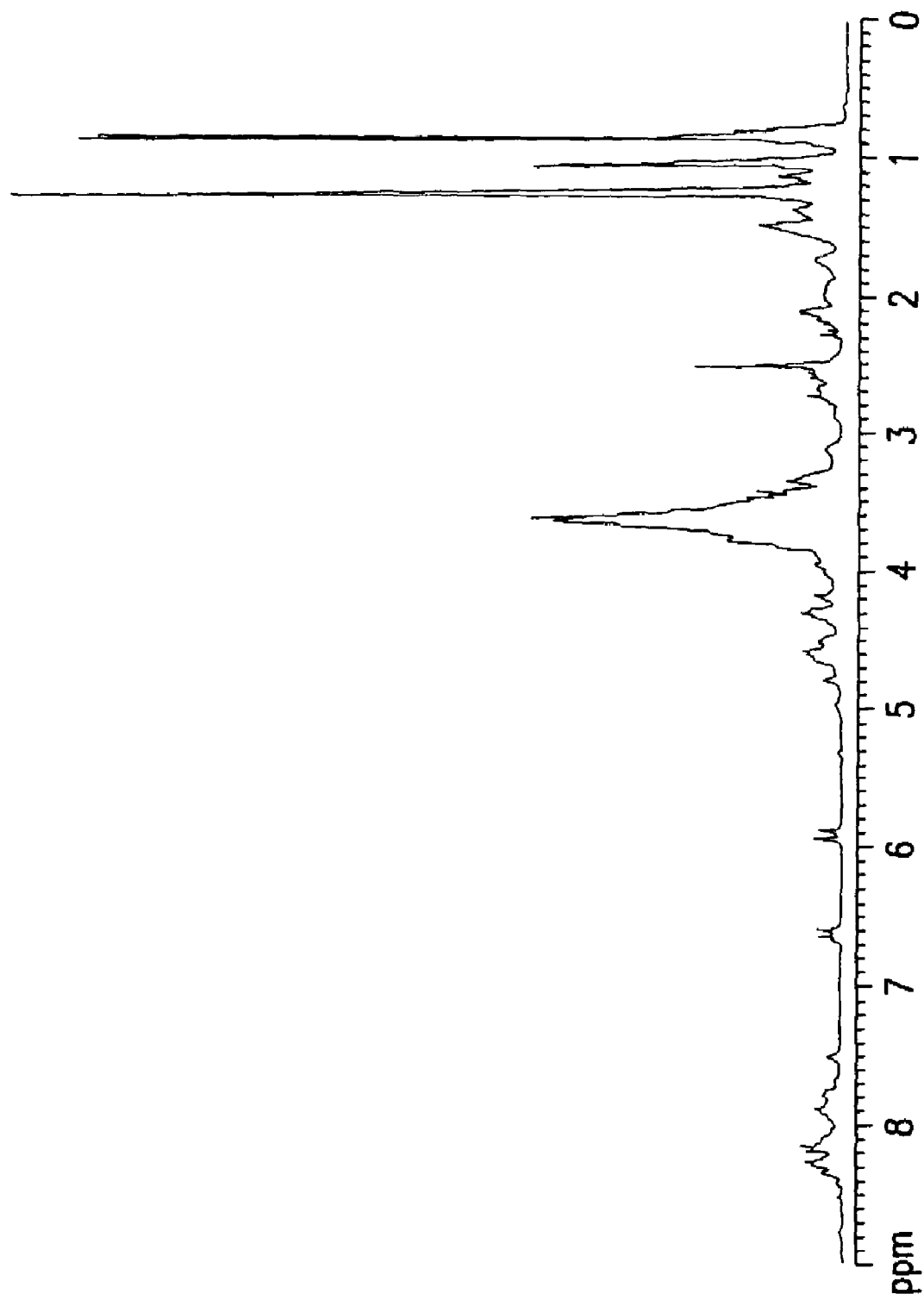
FIG. 2. Characteristic proton nuclear magnetic resonance (NMR) spectrum of compound designated AW998B in DMSO-$d_6$ at 300 MHz.

The physico-chemical characteristics of AW998B are as follows:
a) Apparent Molecular Formula: $C_{58}H_{92}N_{12}O_{19}$
b) Molecular Weight: Positive Ion Electrospray MS m/z=1261.5 (M+H)$^+$; HRMS (FT-ICR): m/z 1261.6683 (M+H)$^+$, calculated 1261.6678
c) Ultraviolet Absorption Spectrum: $\lambda_{max}$ nm (acetonitrile-water): end absorption
d) Specific Rotation: $[\alpha]_D^{25}$ =−19° (c 0.41, MeOH)
e) Proton nuclear magnetic resonance spectrum: (300 MHz DMSO-d$_6$) as shown in FIG. 2.

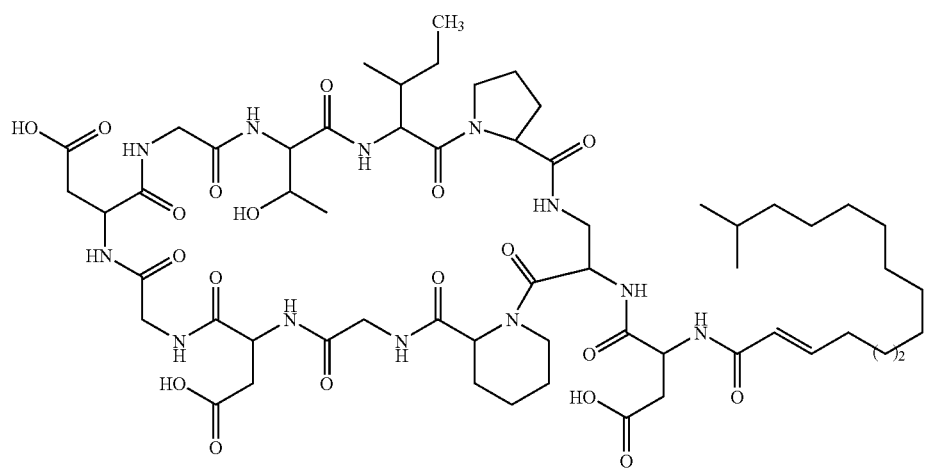

The structure of the new antibiotic AW998C is

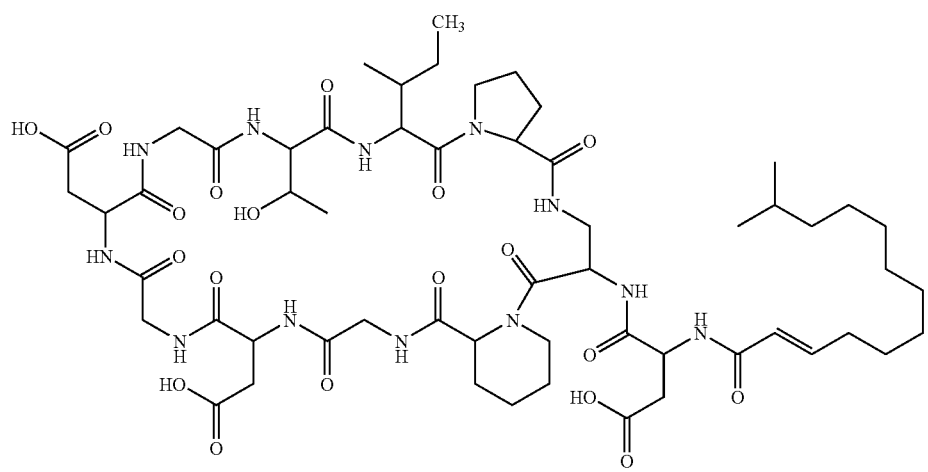

Figure 3:
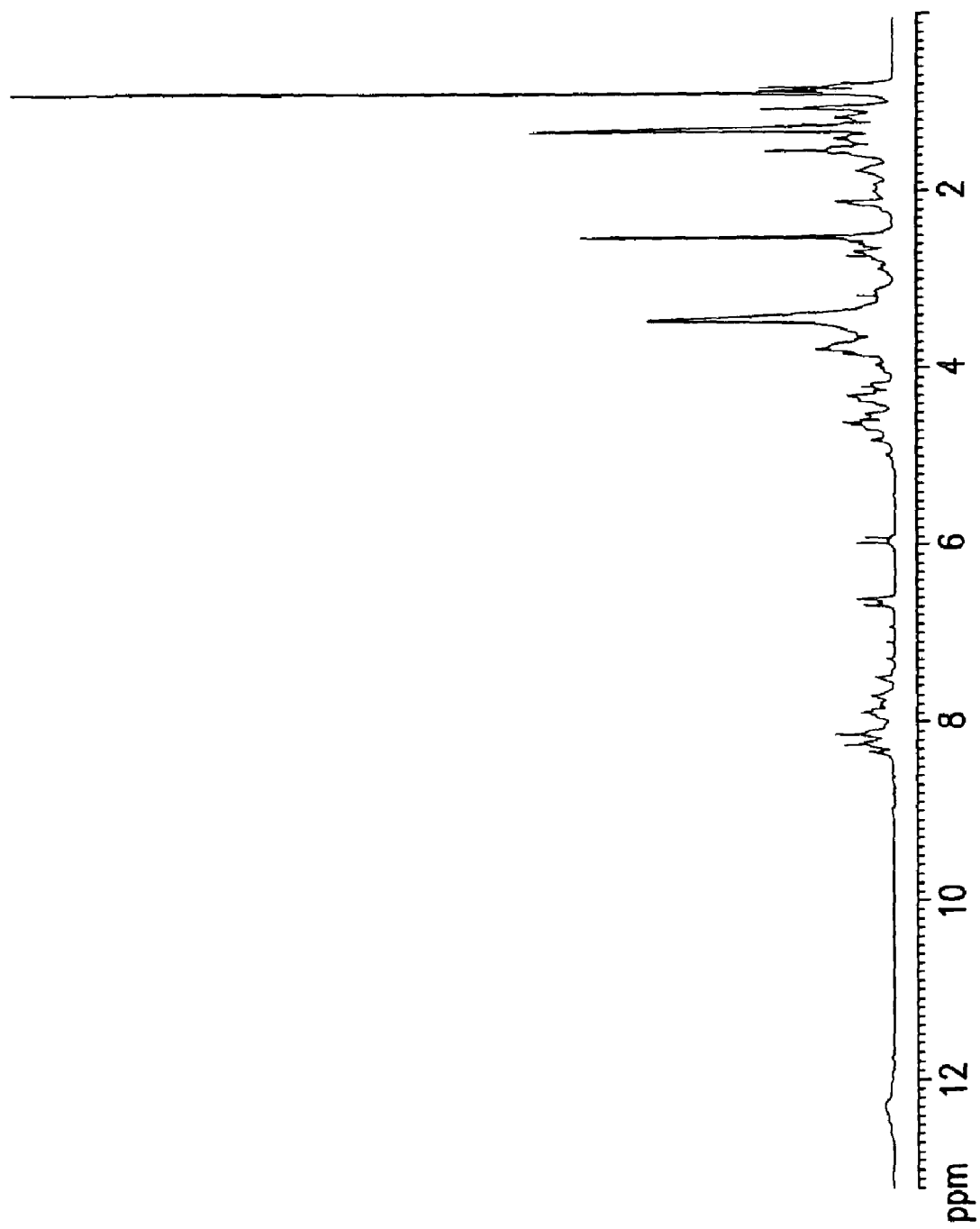
FIG. 3. Characteristic proton nuclear magnetic resonance (NMR) spectrum of compound designated AW998C in DMSO-$d_6$ at 300 MHz.

The physico-chemical characteristics of AW998C are
a) Apparent Molecular Formula: $C_{56}H_{88}N_{12}O_{19}$
b) Molecular Weight: Positive Ion Electrospray MS m/z 1233.4 (M+H)$^+$; High Resolution MS (FT-ICR): m/z 1233.6367 (M+H)$^+$, calculated 1233.6365 measured 1232.6294, calculated 1232.6692 c) Ultraviolet Absorption Spectrum: $\lambda_{max}$ nm (acetonitrile-water): end absorption
d) Specific Rotation: $[\alpha]_D^{25} = -13°$ (c 0.28, MeOH)
e) Proton nuclear magnetic resonance spectrum: (300 MHz DMSO-$d_6$) as shown in FIG. 3.

The structure of the new antibiotic AW998D is

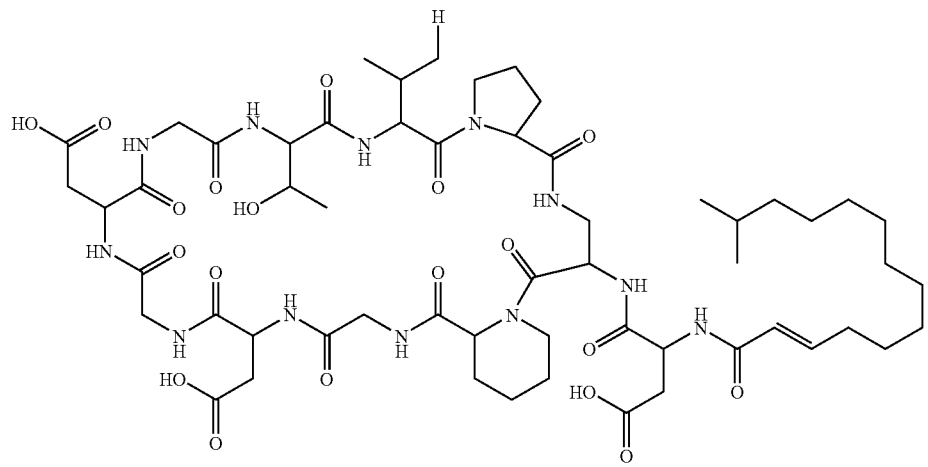

Figure 4:
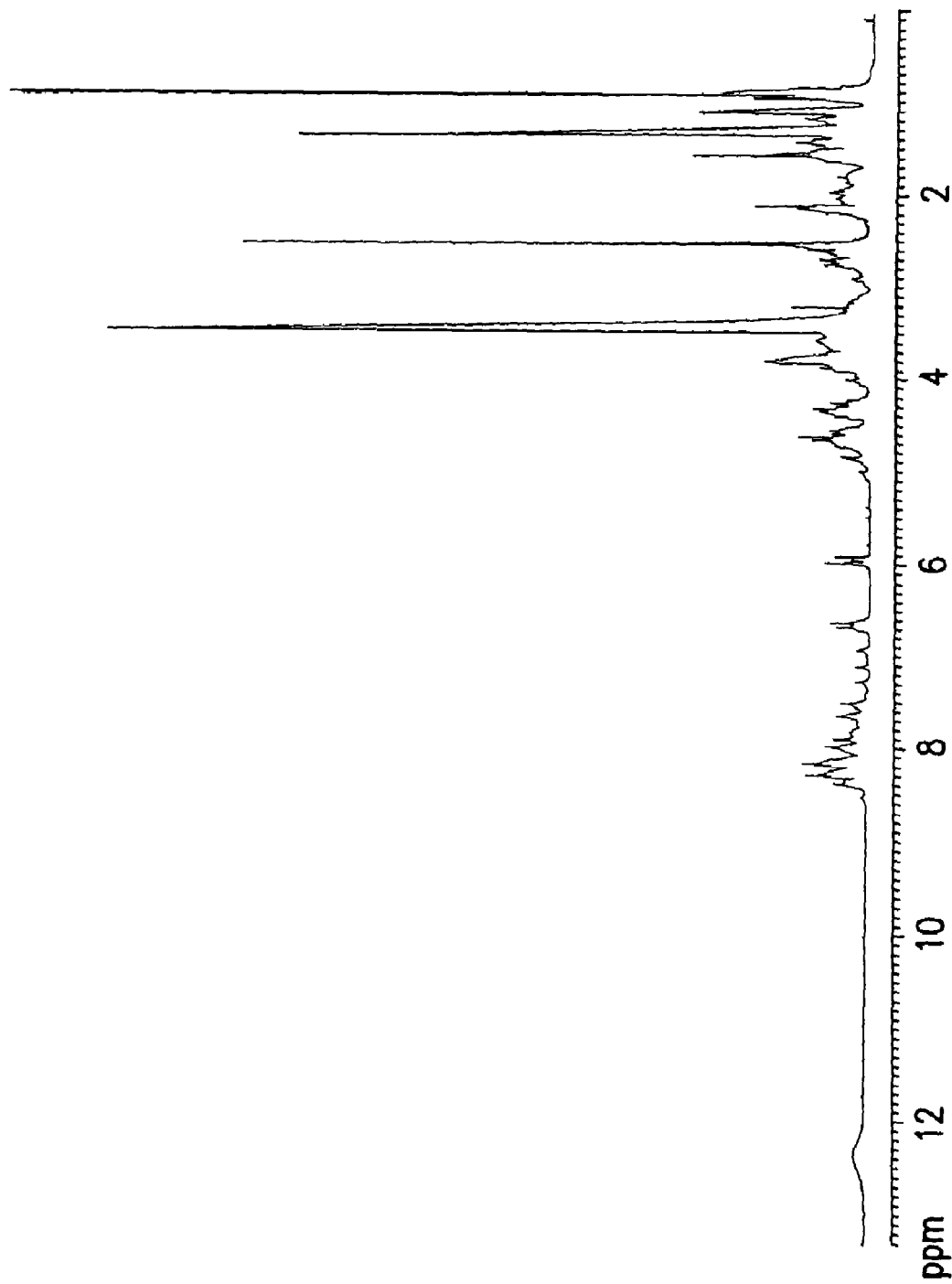
FIG. 4. Characteristic proton nuclear magnetic resonance (NMR) spectrum of compound designated AW998D in DMSO-$d_6$ at 300 MHz.

The physico-chemical characteristics of AW998D are as follows:
a) Apparent Molecular Formula: $C_{56}H_{88}N_{12}O_{19}$
b) Molecular Weight: Positive Ion Electrospray MS m/z=1233.4 (M+H)$^+$; High Resolution MS (FT-ICR) m/z 1233.6356 (M+H)$^+$, calculated 1233.6365 for $C_{56}H_{89}N_{12}O_{19}$
c) Ultraviolet Absorption Spectrum: $\lambda_{max}$ nm (acetonitrile-water): end absorption
d) Specific Rotation: $[\alpha]_D^{25} = -18°$ (c 0.33, MeOH);
e) Proton nuclear magnetic resonance spectrum: (300 MHz DMSO-$d_6$) as shown in FIG. 4.

The new antibacterial agents AW998A, AW998B, AW998C and AW998D are formed during cultivation under controlled conditions of a new strain of *Streptomyces* species designated LL-AW998.

This microorganism is maintained in the culture collection of Wyeth Research, Pearl River, N.Y. 10965, as culture LL-AW998. A viable culture of this microorganism is deposited under the Budapest Treaty with the Patent Culture Collection Laboratory, Northern Regional Research Center, U.S. Department of Agriculture, Peoria, Ill. 61604, and added to its permanent collection. Culture LL-AW998 has been assigned the NRRL accession # 30605.

For the production of these new antibacterial agents AW998A, AW998B, AW998C and AW998D the present invention is not limited to this particular organism. In fact, it is desired and intended to include the use of naturally-occurring mutants of this organism, as well as induced mutants produced from this organism by various mutagenic means known to those skilled in the art, such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techniques known to those skilled in the art such as for example, conjugation, transduction and genetic engineering techniques.

Culture LL-AW998 produces aerial mycelium with black to grey spores. The substrate mycelium is brown and a brown soluble pigment is produced. The 16S rDNA sequence was determined for strain LL-AW998 following isolation and direct sequencing of the amplified gene. The nucleotide sequence was aligned with the sequences of previously studies *streptomycetes*, and phylogenetic trees were generated by using two neighbor-joining tree algorithms. The 16S rDNA sequence supported classification of the strain in the genus *Streptomyces*.

It is a further object of the invention to provide a method of treating bacterial infections in mammals in need thereof with an effective amount of a compound selected from the group AW998A, AW998B, AW998C and AW998D or a combination thereof and pharmaceutically acceptable salts thereof.

It is an additional object of the invention to provide a pharmaceutical composition of a compound selected from the group AW998A, AW998B, AW998C and AW998D or combinations thereof and pharmaceutically acceptable salts thereof in the presence of one or more pharmaceutically acceptable carriers.

Biological Activity

Standard IN VITRO Antibacterial Pharmacological Test Procedures

The minimum inhibitory concentration (MIC), the lowest concentration of the antibiotic which inhibits growth of the test organism, is determined by the broth dilution method using Muller-Hinton II agar (Baltimore Biological Laboratories) following the recommendations of the National Committee for Clinical Laboratory Standards [Methods for dilution antimicrobial susceptibility tests for bacteria that grow aerobically, approved standard M7-A2, National Committee for Clinical Laboratory Standards, Villanova, Pa.].

An inoculum level of $5 \times 10^5$ CFU/mL, and a range of antibiotic concentrations (64–0.06 μg/mL) is used. The MIC is determined after the microtiter plates are incubated for 18 hours at 35° C. in an ambient air incubator. The test organisms include a spectrum of Gram-positive bacteria comprised of *Staphylococcus* sp., *Streptococcus* sp. and *Enterococcus* sp.

The test organisms also include a spectrum of Gram-negative bacteria comprised of *E. coli* GC, *M. catarrhalis* and *H. influenzae*.

IN VITRO Evaluation of AW998 Compounds as Antibacterial Agents

The in vitro antibacterial activity of AW998A, AW998B, AW998C and AW998D is determined against a spectrum of Gram-positive and Gram-negative bacteria by a standard broth dilution method. Serial dilution of the compounds are made in Mueller-Hinton broth and inoculated with a bacterial suspension. The lowest concentration of compound that inhibited the growth of a bacterial strain after 18 hours of incubation at 35° C. is reported as the minimal inhibitory concentration (MIC) for that strain. The results are given in Table 1.

TABLE 1

Antimicrobial Activity (MIC, μg/mL) of AW998-A to -D

|  | AW998A | AW998B | AW998C | AW998D |
|---|---|---|---|---|
| S. aureus GC 1131 (MRSA) | 16 | 8 | 128 | 128 |
| S. aureus GC 4543 (Smith) | 8 | 4 | 64 | 128 |
| S. aureus GC 2216 (ATCC) | 8 | 4 | 64 | 128 |
| E. faecalis GC 4555 (ATCC) | 32 | 8 | 128 | 128 |
| E. faecalis GC 2242 (VRE) | 64 | 16 | 128 | 128 |
| S. pneumoniae GC 1894* (5% LHB) | 4 | 1 | 8 | 16 |
| S. pneumoniae GC 1894+ (THY) | 2 | 2 | 64 | 128 |
| C. albicans GC 3066 (Yeast) | 128 | 64 | >128 | >128 |
| E. coli GC 4559 (wt) | >128 | >128 | >128 | >128 |
| E.coil GC 4560 (imp) | 32 | 32 | >128 | >128 |
| B. subtilis GC 6344 (168) | 32 | 8 | 128 | 128 |
| M. catarrhalis GC 6907* (clinical) | >128 | >128 | >128 | >128 |
| H. influenzae GC 6896 <> (ATTC) | >128 | >128 | >128 | >128 |

The antibacterial results show that the products according to the invention have a broad spectrum of activity against the bacterial strains tested.

Antibiotics AW998A, AW998B, AW998C and AW998D derive their utility from their antibacterial activity. For example, these compounds may be used in the suppression of bacterial infections, as a topical antibacterial agent or as a general disinfectant. These compounds are not limited to the uses listed. The rapid lethal action on germs of the products of the invention enables them to be used as surface disinfectants. In disinfectant use for inert surfaces the compounds of this invention may be formulated in combination with acceptable carriers appropriate for the intended use. Carriers are not limited to aqueous or non-aqueous detergent solutions or sprays, but also include a variety of organic solvents and may further include an alcohol (ethanol, isopropanol). In therapeutic use, the compounds of this invention may be administered in the form of conventional pharmaceutical compositions appropriate for the intended use. Such compositions may be formulated as to be suitable for oral, parental or topical administration. The active ingredient may be combined in admixture with one or more nontoxic pharmaceutical carriers that may take a variety of forms depending on the form of preparation desired for administration, i.e. Oral, parental, or topical.

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parentally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 0.001 mg/kg of body weight to 100.0 mg/kg of body weight should be administered one to five times per day via any typical route of administration including but not limited to oral, parental (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the antibacterially effective amount of the antibiotics of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the antibiotics of the invention.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. These active compounds may also be administered parentally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition which comprises a compound of this invention in combination or association with one or more pharmaceutically acceptable carriers. In particular, the present invention provides a pharmaceutical composition which comprises an antibacterially effective amount of a compound of this invention or combinations thereof and a pharmaceutically acceptable carrier.

The present invention further provides a method of treating bacterial infections in warm-blooded animals including man, which comprises administering to the afflicted warm-blooded animals an antibacterially effective amount of a compound or a pharmaceutical composition of a compound of the invention or combinations thereof. The invention will be more fully described in conjunction with the following specific examples which are not to be construed as limiting the scope of the invention.

Pharmaceutically acceptable salts of the compounds of the invention include basic salts of inorganic and organic acids, including but not limited to hydrochloric acid, hydrobromic acid, sulphuric acid, phosphoric acid, nitric acid, methanesulfonic acid, ethanesulfonic acid, benzenesulfonic acid, toluenesulfonic acid, napthalenesulfonic acid, camphorsulfonic acid, malic acid, acetic acid, trifluroacetic acid, oxalic acid, malonic acid, tartaric acid, citric acid, lactic acid, fumaric acid, succinic acid, maleic acid, salycylic acid, benzoic acid, phenylacetic acid, mandelic acid and the like.

When compounds of the invention include an acidic function such as a carboxy group, then suitable pharmaceutically acceptable salts of the compounds of the invention with an acidic moiety can be formed from organic and inorganic bases. Such includes but is not limited to salts formed with alkali metals or alkaline earth metals such as sodium, potassium, lithium, calcium, or magnesium or organic bases such as triethylamine, N,N-diethylmethylamine, N,N-diethylethylenediamine, and N-tetraalkylammonium salts such as N-tetrabutylammonium salts. For additional examples of "pharmaceutically acceptable salts" see Berge et al, J. Pharm. Sci. 66, 1 (1977).

General Fermentation Conditions

Cultivation of *Streptomyces* designated LL-AW998 may be carried out in a wide variety of liquid culture media. Media which are useful for the production of AW998A, AW998B, AW998C, and AW998D include an assimilable source of carbon, such as dextrin, sucrose, molasses, glycerol, etc.; an assimilable source of nitrogen, such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicon oil may be added as needed.

General Procedure for the Isolation of AW998A, AW998B, AW998C and AW998D.

The AW998A, AW998B, AW998C and AW998D are recovered from the fermentation broth by partitioning with butanol or adsorption on HP20 resin followed by elution with organic solvents which include methanol and acetonitrile to afford crude products.

The crude products are then separated into the AW998A, AW998B, AW998C and AW998D components which are further purified by high performance liquid chromatography (HPLC) on a reverse-phase column using acetonitrile-water solutions containing trifluoroacetic acid or solutions of methanol-acetonitrile.

The invention will be further described in conjunction with the following non-limiting examples.

General Fermentation Conditions

EXAMPLE 1

Culture Preservation

Culture LL-AW998 is preserved as frozen whole cells (frozen vegetative mycelia, FVM) prepared from cells grown for 72 hours in ATCC medium 172 (Dextrose 1%, Soluble Starch 2%, Yeast Extract 2%, and N-Z Amine Type A 0.5%, pH 7.3). Glycerol is added to 20% and the cells are frozen at $-150°$ C.

| A seed medium of the following formulation is prepared: | |
|---|---|
| Dextrose | 1% |
| Soluble starch | 2% |
| Yeast extract | 2% |
| N–Z Amine Type A (Sheffield) | 5.0% |
| pH | 7.3 |

Fifty ml of seed medium in a 250 Erlenmeyer shake flask is inoculated with cells of LL-AW998 cultured on ATCC agar medium #172 (ATCC Media Handbook, $1^{st}$ edition, 1984). Sufficient inoculum from the agar culture is used to provide a turbid seed after 72 hours of growth. The primary seed flask is incubated at 28° C., 200 rpm using a gyro-rotary shaker with a 2 inch throw, for 72 hours. The primary seed (20% inoculum) is then used to inoculate five 250 ml Erlenmeyer flasks containing 50 ml of medium 172. These secondary seed flasks are incubated at 28° C., 200 rpm using a gyro-rotary shaker (2" stroke), for 72 Hours.

EXAMPLE 2

Production Tank Fermentation

| A fermentation production medium of the following formulation is prepared: | |
|---|---|
| Soy Flour | 1.25% |
| N–Z Amine (Sheffield Type A) | 0.25% |
| Dextrose | 1.25% |
| $CaCO_3$ | 0.1% |
| $NH_4Cl$ | 0.15% |
| pH | 6.8 |

Fifteen L glass jar fermentors are prepared with 10L of the above production medium and inoculated with 250 ml (2.5%) of the secondary seed fermentation and incubated at 28° C. for 6 days at 600 rpm with 10L/min airflow.

General Procedure for Purification of AW998 Components

Antibiotics AW998A, AW998B, AW998C and are purified from the cultured broth of organism LL-AW998. The antibiotics are recovered from the clarified broth by 1) partitioning against n-BuOH, or 2) adsorption onto HP20 resin followed by desorption from the resin using mixtures of organic solvents which include methanol and acetonitrile and water. The residues remaining after removal of the solvents are purified by high pressure liquid chromatography (HPLC) on reversed-phase ODS(Octadecylsilane) support, typically using mobile phases comprised of acetonitrile-water combinations with small amounts of trifluoroacetic acid. Methanol may be substituted for acetonitrile as mobile phase in HPLC purifications. The antibiotics eluted in the following sequence: AW998-C, AW998-D, AW998-A, and AW998-B. All compounds were finally obtained as a white amorphous powder after lyophilization.

The invention is further described in conjunction with the following non-limiting examples. All components may be purified from the complex in a manner similar to the examples given.

EXAMPLE 3

Purification of the AW998 Antibiotics from Fermentation Broth

The antibiotics AW998A, AW998B, AW998C and AW998D are purified as follows: One liter of the fermentation broth of LL-AW998 culture from example 2 is centrifuged. The aqueous layer is partitioned against n-BuOH (500 mL×2) and the mycelium mass is extracted with MeOH (100 mL×2). The activity mostly went to the n-BuOH layer based on *Staphylococcus aureus* assay. Both n-BuOH and MeOH extracts are combined and concentrated under reduced pressure to dryness affording a residue. The dried residue is redissolved in N,N-dimethylformamide (DMF)-MeOH-H$_2$O (2:1:1) and loaded onto a reversed phase HPLC column (MetaChem ODS-3, 20 mm×250 mm). The column is washed with a gradient of 50–70% acetonitrile in 0.05% trifluoroacidic acid buffer over 60 minutes at a flow rate of 7 mL/min, and the peaks are detected by UV absorbance at 215 nm. The antibiotics are eluted in the following retention times in minutes: 34 minutes for AW998-C, 38 minutes for AW998-D, 46 minutes for AW998-A, and 55 minutes for AW998-B. The major components AW998-A (70 mg) and AW998-B (15 mg) are obtained in 95–98% purity as assessed by $^1$H NMR analysis. A second HPLC purification of the minor components AW998-C and AW998-D using the same HPLC column with a gradient elution of 40–60% acetonitrile in 0.05% TFA buffer over 90 minutes gives pure AW998-C (9.3 mg, 61 minutes) and AW998-D (9.5 mg, 68 minutes).

What is claimed is:

1. The compound AW998A which has the structure:

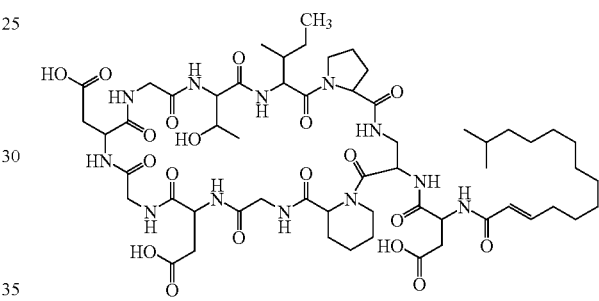

2. The compound AW998B which has the structure:

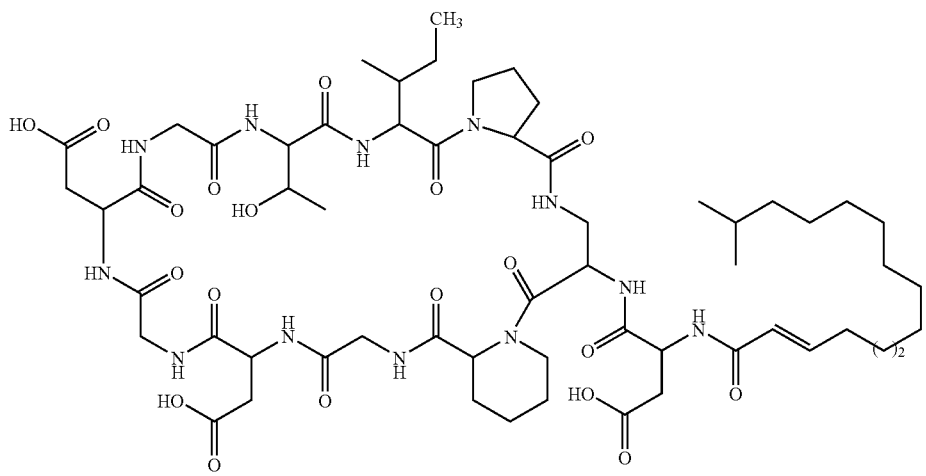

3. The compound AW998C which has the structure:

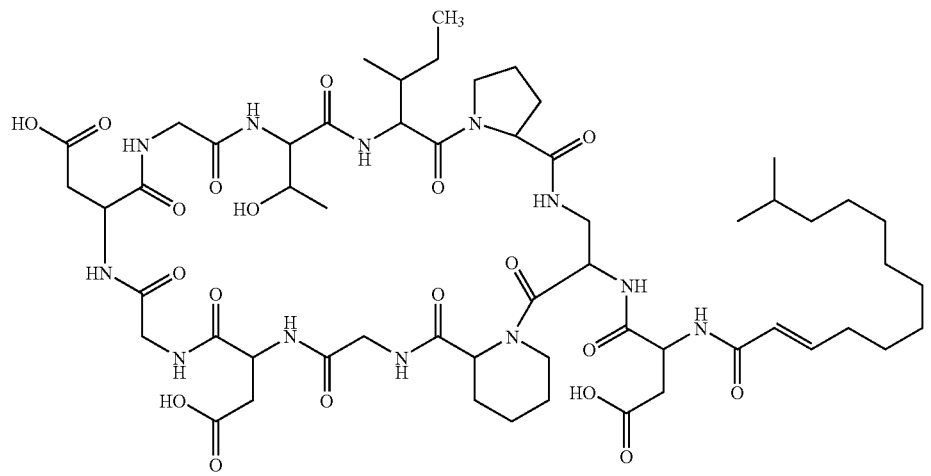

4. The compound AW998D which has the structure:

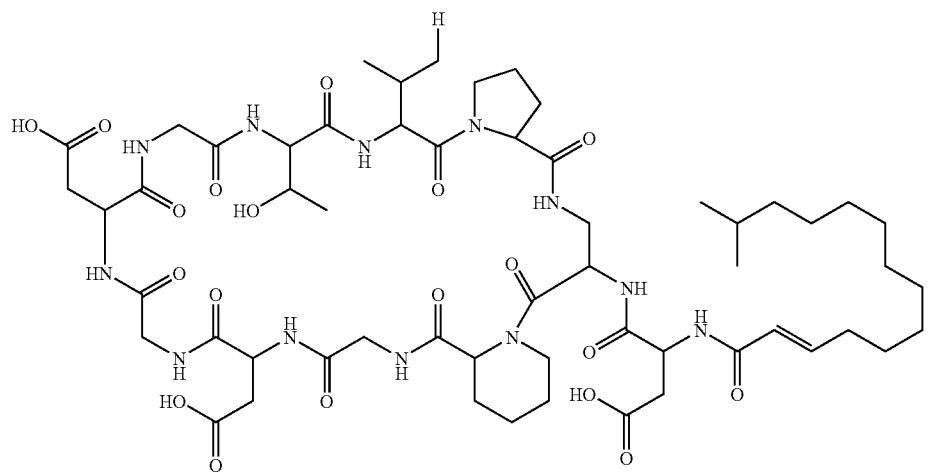

5. A method of treating a warm-blooded animal affected by bacterial infections, which method comprises administering to said warm-blooded animal in need thereof an effective amount of a compound selected from the group AW998A, AW998B, AW998C and AW998D or combinations thereof.

6. A pharmaceutical composition comprising an effective amount of a compound selected from the group AW998A, AW998B, AW998C and AW998D or combinations thereof together with one or more pharmaceutically acceptable carriers.

7. A process for the preparation of a compound selected from the group AW998A, AW998B, AW998C and AW998D or combinations thereof which comprises cultivating *Streptomyces* designated LL-AW998 under aerobic conditions, in a sterile liquid medium containing assimilable sources of carbon, nitrogen and inorganic anion and cation salts, until substantial antibiotic activity is imparted to said medium by the production of a compound selected from the group AW998A, AW998B, AW998C and AW998D, or combination thereof, recovering and isolating compounds selected from the group AW998A, AW998B, AW998C and AW998D or combinations thereof.

8. A disinfectant composition comprising an effective amount of a compound selected from the group AW998A, AW998B, AW998C and AW998D or combinations thereof together with one or more acceptable disinfectant carriers.

9. A process according to claim 7 wherein the assimilable sources of carbon, nitrogen and inorganic anion and cation salts are Soy Flour 1.25%, N-Z Amine, (Sheffield Type A) 0.25%, Dextrose 1.25%, $CaCO_3$ 0.1%, and $NH_4Cl$ 0.15%.

* * * * *